(12) United States Patent
Parizot

(10) Patent No.: US 7,556,608 B2
(45) Date of Patent: Jul. 7, 2009

(54) DEVICE FOR SUPPORTING LUMBAR VERTEBRAS AND/OR SACROSPINAL MUSCLES

(76) Inventor: Jean-Paul Parizot, 17, place d'Arcy, 21000 Dijon (FR)

( * ) Notice: Subject to any disclaimer, the term of this patent is extended or adjusted under 35 U.S.C. 154(b) by 0 days.

(21) Appl. No.: 10/541,133

(22) PCT Filed: Dec. 30, 2003

(86) PCT No.: PCT/FR03/03941

§ 371 (c)(1),
(2), (4) Date: Dec. 23, 2005

(87) PCT Pub. No.: WO2004/060218

PCT Pub. Date: Jul. 22, 2004

(65) Prior Publication Data

US 2006/0129077 A1 Jun. 15, 2006

(30) Foreign Application Priority Data

Dec. 30, 2002 (FR) .................................. 02 16835

(51) Int. Cl.
*A61F 13/00* (2006.01)
(52) U.S. Cl. ....................................... 602/19; 128/96.1
(58) Field of Classification Search .................. 602/19, 602/18, 20, 23, 26, 60–64; 128/96.1, 100.1, 128/101.1, 99.1; 2/311, 312; D24/190
See application file for complete search history.

(56) References Cited

U.S. PATENT DOCUMENTS

| 4,750,480 | A | * | 6/1988 | Jenness | 602/19 |
| 4,768,499 | A | | 9/1988 | Kemp | |
| 5,533,961 | A | * | 7/1996 | Iwata | 602/19 |
| 6,322,529 | B1 | * | 11/2001 | Chung | 602/19 |
| 6,500,137 | B1 | * | 12/2002 | Molino et al. | 602/19 |
| 6,676,620 | B2 | * | 1/2004 | Schwenn et al. | 602/19 |
| 2003/0050584 | A1 | * | 3/2003 | Toda | 602/19 |

FOREIGN PATENT DOCUMENTS

FR 2745490 9/1997

* cited by examiner

Primary Examiner—Kim M Lewis
(74) Attorney, Agent, or Firm—Blakely, Sokoloff, Taylor & Zafman LLP

(57) ABSTRACT

This invention relates to a device for supporting lumbar vertebras and/or sacrospinal muscles, generally called a lumbar belt. The inventive device comprises a back lumbar supporting part (1) and two lateral parts (2a, 2b) which are connected to the said back part (1) and provided with additional closing means (12b) arranged on the free front ends thereof. The external surface of the back part (1) comprises fixing means which interact with additional fixing means (9a, 9b) connected to the free back ends of the lateral parts (2a, 2b) in such a way that it is possible to close the belt without overlapping the said lateral parts (2a, 2b) on the abdominal region of a patient.

15 Claims, 2 Drawing Sheets

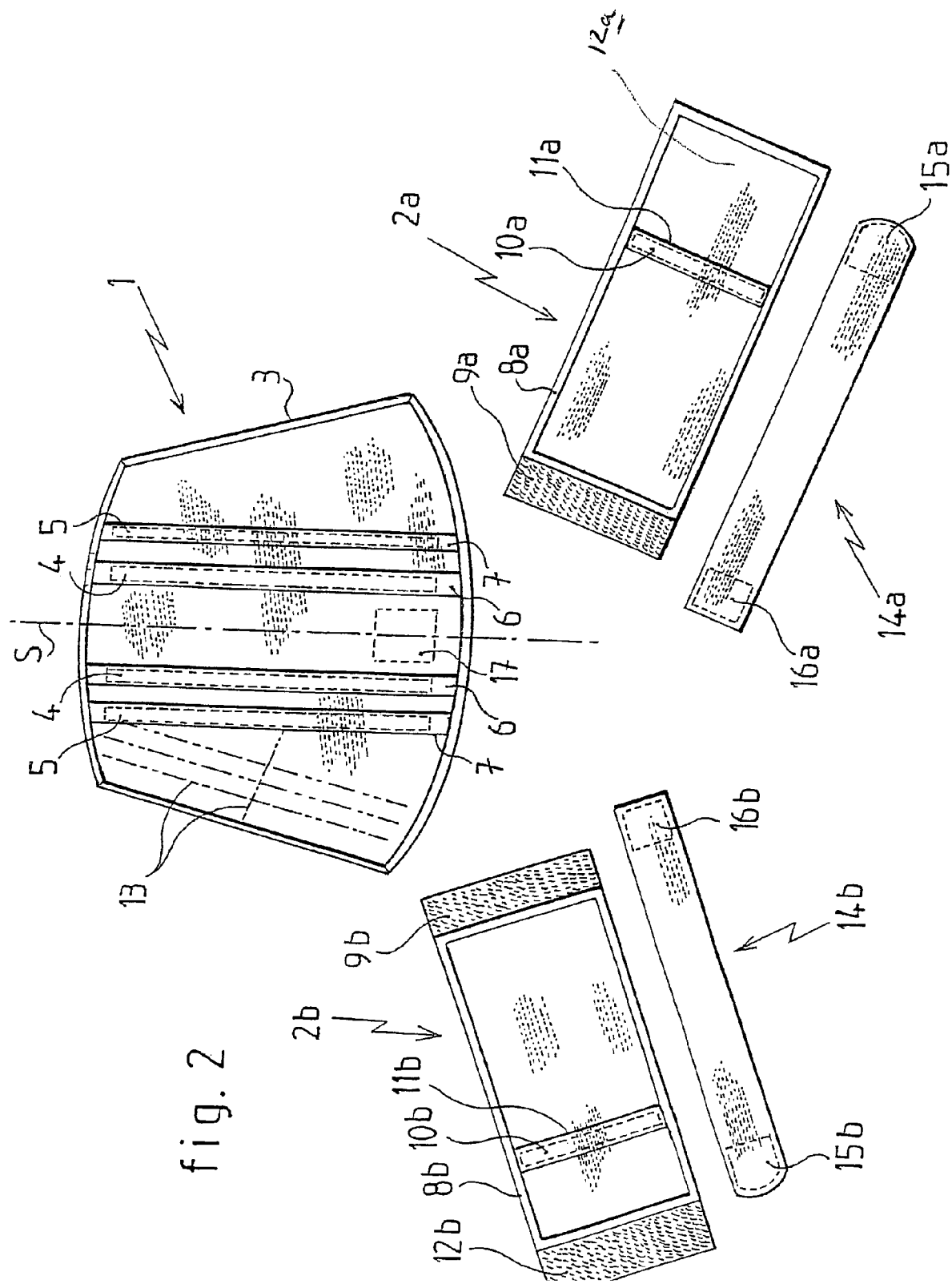

DEVICE FOR SUPPORTING LUMBAR VERTEBRAS AND/OR SACROSPINAL MUSCLES

Figure 1:
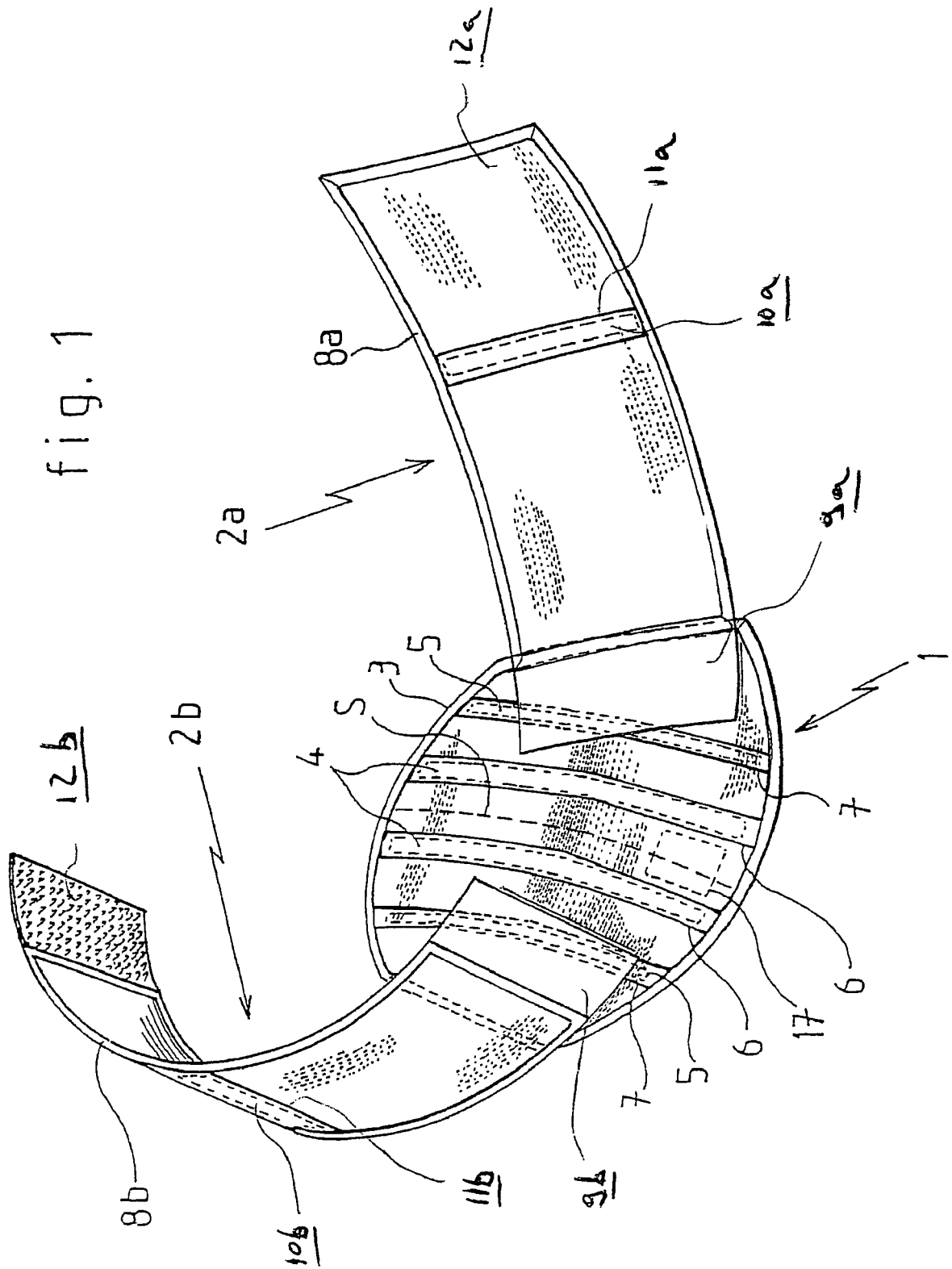

The present patent application is a non-provisional application of International Application No. PCT/FR2003/003941, filed Dec. 30, 2003.

This invention relates to a device for supporting lumbar vertebras and/or sacrospinal muscles commonly called a lumbar belt.

In the field of orthopaedic devices, so-called lumbar belts designed to treat lumbar pain caused by isolated lumbopelvic strain or repeated stresses on lumbopelvic anatomic structures are well known. Furthermore, it is well known that these lumbar belts can be worn to reinforce the abdominal belt for post-surgical support or temporary support of the abdominal belt during strain or reeducation periods, etc.

Most of these lumbar belts are composed of a posterior lumbar support part and two lateral parts fixed to the posterior part and provided with additional separable closing means on the abdomen such as for example Velcro (registered trademark) at their front free ends. For example, this is the case for American patent U.S. Pat. No. 4,768,499 that describes a support belt for back and abdominal muscles. The belt includes a posterior non-padded central part made from leather and positioned in the hollow of the back to cover the five lumbar vertebras and sacrospinal muscles on each side of the lumbar vertebras. The ends of the belt extend starting from the posterior central part such that the said ends are fixed together around the patient's abdominal muscles. Thus, the posterior central part bears in contact with the lumbar zone pressing forwards in a position that restrains the sacrospinal muscles and applies pressure on the lumbar vertebras to prevent them from relaxing, that could cause pain in the lower part of the patient's spinal column.

These lumbar belts have the disadvantage that they create an extra-thickness on the abdominal belt when they are opened, the two lateral parts of the belt provided with self-gripping type closing means, for example such as "Velcro", overlapping to close the said belt, which is uncomfortable for the patient.

Therefore one of the purposes of the invention is to overcome this disadvantage by proposing a simple and inexpensive design for a lumbar belt to close the belt without overlapping of the lateral parts on the patient's abdominal area.

To achieve this, the invention proposed a device for supporting lumbar vertebras and/or sacrospinal muscles, commonly called a lumbar belt, and comprising a posterior lumbar support part and two lateral parts fixed to the posterior part and provided with additional closing means at their free front ends, remarkable in the outside face of the posterior part includes attachment means that can cooperate with additional attachment means fixed to the free back ends of the lateral parts in order to close the belt without the lateral parts overlapping on the patient's abdominal area.

It can clearly be understood that unlike devices according to prior art, the dimensions of the lumbar belt are adjusted on the posterior lumbar support part, in other words in the patient's back and not at the front free ends of the lateral parts on the abdominal area of the said patient.

Other advantages and characteristics will become clear after reading the following execution variant given as a non-limitative example of the device for supporting lumbar vertebras in accordance with the invention referenced with the attached drawings in which:

FIG. 1 shows a perspective view of the device for supporting lumbar vertebras according to the invention, FIG. 2 is a top view of elements of the lumbar vertebras support device according to the invention when developed.

With reference to FIGS. 1 and 2, the device for supporting lumbar vertebras or sacrospinal muscles is composed of a posterior lumbar support part 1 and two lateral parts 2a and 2b that will be described in detail later. The posterior part 1 is obtained from a fabric and it has a globally trapezoidal shape, the large and the small base of the posterior part 1 being convex to match the curvature of the patient's body on which the lumbar vertebra support device is put into place. It will be noted that the small and the large base respectively form the upper part and the lower part respectively of the said posterior part 1. The posterior part is advantageously obtained from a longitudinally resilient fabric to provide setting in the lumbopelvic region. Moreover, the said posterior part 1 comprises a braid 3 at its periphery to prevent it from fraying, the said braid 3 being slightly resilient. The posterior part 1 is provided with loops on its outside face that does not bear on the patient's body, capable of cooperating with additional Velcro (registered trademark) type closing mean hooks fixed to the free back end of the lateral parts 2a and 2b.

Furthermore, the posterior part 1 also comprises four transverse whalebones extending parallel to each other from the small base to the large base of the posterior part 1 and uniformly distributed on each side of the axis of symmetry S of the said posterior part 1. Thus, the posterior part 1 comprises two central whalebones 4 and two external whalebones 5 extending in sheaths 6 and 7 respectively sewn on the outside face of the posterior part. 1 so as to not make the patient uncomfortable. It will be seen that the term "central whalebones" 4 refers to the whalebones extending close-to the axis of symmetry S of the posterior part 1. The sheaths 7 of the external whalebones 5 are obtained from a fabric with loops that can cooperate with the hooked closing means of the lateral parts 2a, 2b, as will be seen later. Furthermore, the sheaths 6 of the central whalebones are made from a smooth material such that the lateral parts 2a, 2b cannot be fixed adjacent to the said central whalebones 4. Furthermore, the central whalebones 4 and the external whalebones 5 of the posterior part 1 are advantageously curved such that the outside face of the posterior part 1 is concave and that the inside face, in other words the face bearing on the patient's lumbar areas, of the said posterior part 1 is convex to match the natural curvature of the lower part of the back.

The lateral parts 2a, 2b referenced in FIGS. 1 and 2 are composed of a strip of rectangular fabric provided with braids 8a and 8b respectively at its periphery to prevent it from fraying. Each lateral part 2a, 2b comprises a strip of fabric 9a and 9b respectively at one of its ends called the free back end, provided with hooks that can cooperate with the loops of the outside face of the posterior part 1. These fabric strips 9a, 9b are sewn to the free back ends of the lateral part 2a and 2b respectively. Each lateral part 2a, 2b comprises a transverse whalebone close to its front free end called the abdominal support whalebone 10a and 10b respectively that extends in a sheath 11a and 11b respectively sewn on the outside face of the lateral parts 2a and 2b respectively.

In the same way as above, the lateral parts 2a and 2b are advantageously made from a fabric with loops 12a on its outside face, in other words the face of the lateral parts 2a and 2b that do not come into contact with the patient's skin, the loops cooperating with additional hooked type closing means 12b such as Velcro (registered trademark).

This fabric is also advantageously resilient in the longitudinal direction.

One of the lateral parts 2a, 2b, in this particular example embodiment (in fact the left lateral part 2b) comprises a fabric strip 12b at its front free end provided with additional closing means of the sewn hooks type at the said free end of the lateral part 2b. Thus, the lateral parts 2a, 2b are fixed to the posterior part 1 by closing means 9a, 9b such that the transverse edges of the parts 2a, 2b extend parallel to the transverse edges of the posterior part 1, the free ends of the lateral parts 2a and 2b respectively preferably being positioned between the central whalebones 4 and the transverse edges of the said posterior part 1. It will be observed that the back ends of the lateral parts cannot be fixed to the posterior part 1 beyond the central whalebones 4 for which the sheath 6 obtained from a smooth material prevents fixing of the lateral parts 2a and 2b respectively.

In one particularly advantageous manner, the outside face of the posterior part 1 comprises marking lines 13 extending parallel to and/or perpendicular to the lateral edges of the posterior part 1, the said lines being shown as chain dotted lines in FIG. 2.

These lines assure the patient that the transverse edges of the lateral parts 2a and 2b are well aligned and are parallel to the transverse edges of the posterior part 1.

Accessorily, the device for supporting lumbar vertebras and/or sacrospinal muscles comprises two secondary lateral parts 14a, 14b composed of two narrow rectangular fabric strips obtained from a longitudinally elastic fabric and provided with loops capable of cooperating with additional hooked closing means on one of its faces corresponding to the outside face of these secondary lateral parts 14a, 14b. These secondary lateral parts 14a, 14b are slightly shorter than the lateral parts 2a and 2b. Furthermore, these secondary lateral parts 14a, 14b include self-gripping attachment means 15a, 16a and 15b, 16b on their inside face at their slightly rounded front and back free ends, of the hooked type capable of cooperating with loops on the outside face of the said secondary lateral parts 14a, 14b and/or lateral parts 2a, 2b respectively and/or loops on the outside face and the posterior part.

Thus, a first secondary lateral part is fixed in the lower part of the posterior part 1, between the central whalebones 4 in an area 17 shown in dashed lines in FIG. 2 such that the first lateral part 14a extends globally perpendicular to the right transverse edge of the posterior part 1, in other words parallel to the lateral part 2a. The back end of the second secondary lateral part 14b is then fixed on the upper face of the first secondary lateral part 14a above the area 17 for attachment of the posterior part 1 such that the second secondary lateral part 14b extends perpendicular to the second left lateral part of the posterior part 1 parallel to the lateral part 2b, and the lateral parts 2a and 2b and the lateral parts 14a and 14b, extend parallel to the axis of symmetry S of the said posterior part. The free front ends of the secondary lateral parts 14a, 14b are then fixed to the outside face of the lateral part 2a, 2b such that the said secondary lateral parts 14a, 14b are tensioned so as to obtain an additional pressure point facing the area 17 on the patient's lumbar vertebras.

Obviously, the attachment means and the additional attachment means of the posterior part 1, the lateral parts 2a, 2b and the secondary lateral parts 14a, 14b may consist of any known attachment means such as self-gripping, hook/hook or similar attachment means.

Moreover, it is quite obvious that the loops on the outside faces of the posterior part 1 and/or the principal lateral parts 2a, 2b and/or secondary parts 14a, 14b may consist of loops of a fabric strip sewn onto the outside face of the said parts, without going outside the scope of the invention.

Finally, it is obvious that the examples that have just been described above are no more than particular illustrations and that different variants of the device for supporting lumbar vertebras could be designed, without going outside the scope of the invention.

The invention claimed is:

1. Device for supporting lumbar vertebras and/or sacrospinal muscles commonly called a lumbar belt, comprising
    a posterior lumbar support part (1),
    two lateral parts (2a, 2b), each lateral part (2a,2b) being provided with a front free end, a free back end, closing means (12a) and complementary closing means (12b) at their respective front free ends, and with complementary adjustable fixing means (9a, 9b) connected to the free back ends of each lateral parts (2a, 2b),
    an outside face of a posterior part (1) comprising fixing means capable of cooperating with the complementary adjustable fixing means (9a, 9b) connected to the free back ends of the lateral parts (2a, 2b) in such a way that the free back ends of the lateral parts (2a, 2b) are capable of closing the belt without being overlapped on the abdominal region of the patient.

2. Device according to claim 1, characterised in that the posterior part (1) has a globally trapezoidal shape, a large and a small base of the trapezoid being convex, provided with at least four whalebones, two central whalebones (4) and two external whalebones (5) extending transversally from the small base to the large base and distributed on each side of an axis of symmetry (S) of the posterior part (1).

3. Device according to claim 2, characterised in that the central whalebones (4) are fixed on the outside face of the posterior part (1) by a sheath (6) obtained from a smooth material so as to prevent fixing of the lateral parts (2a, 2b) on the said central whalebones (4).

4. Device according to any one of the previous claims, characterised in that each lateral part (2a, 2b) comprises a front end and at least one transverse whalebone (10a, 10b) close to the front end for abdominal support.

5. Device according to claim 1, characterised in that it comprises two secondary lateral parts (14a, 14b) comprising free ends, a middle face, an outside face and attachment means on its free ends, on its inside face (15a, 16a, 15b, 16b) that can cooperate firstly with complementary attachment means on the outside face of the said secondary lateral parts (14a, 14b) and/or on an outside face of the lateral parts (2a, 2b), and secondly with a complementary attachment means of the outside face of the posterior lumbar subpart part (1).

6. Device according to claim 1, characterised in that the posterior lumbar support part and/or the lateral parts (2a, 2b) and/or secondary lateral parts (14a, 14b) are obtained from a longitudinally elastic fabric.

7. Device according to claim 2, characterised in that the central (4) and external (5) whalebones of the posterior part (1) are curved such that the outside face of the posterior part (1) is concave and an inside face of the said posterior part (1) that bears on the patients lumbar vertebras is convex.

8. Device according to claim 5, characterised in that the attachment means of the outside face of the posterior Lumbar support part (1) and/or the lateral parts (2a, 2b) and/or the secondary lateral parts (14a, 14b) and the complementary attachment means (9a, 9b, 15a, 16a, 15b, 16b, 12b) consist of attachment means of the loop/hook or hook/hook type.

9. Device for supporting lumbar vertebras and/or sacrospinal muscles commonly called a lumbar belt, comprising
    a posterior lumbar support part (1), wherein said posterior lumbar support part (1) has a globally trapezoidal shape, a large and a small base of the trapezoid being convex, provided with at least four whalebones, two central whalebones (4) and two external whalebones (5) extending transversally from the small base to the large base and distributed on each side of an axis of symmetry (S) of the posterior part (1), two lateral parts (2a, 2b), each lateral part (2a,2b) being provided with closing means (12a) and complementary closing means (12b) at their respective front free ends, and with complementary adjustable fixing means (9a, 9b) connected to the free back ends of each lateral parts (2a, 2b), the outside face of the posterior part (1) comprising fixing means capable of cooperating with complementary adjustable fixing means (9a, 9b) connected to the free back ends of the lateral parts (2a, 2b) in such a way that the free back ends of the lateral parts (2a, 2b) are capable of closing the belt without being overlapped on the abdominal region of the patient.

10. Device according to claim 9, characterised in that the central whalebones (4) are fixed on the outside face of the posterior part (1) by a sheath (6) obtained from a smooth material so as to prevent fixing of the lateral parts (2a, 2b) on the said central whalebones (4).

11. Device according to any one of claims 9 or 10 characterised in that each lateral part (2a, 2b) comprises at least one transverse whalebone (10a, 10b) close to its front end for abdominal support.

12. Device according to claim 9, characterised in that it comprises two secondary lateral parts (14a, 14b) comprising attachment means on its free ends, on its inside face (15a, 16a, 15b, 16b) that can cooperate firstly with complementary attachment means on the outside face of the said secondary lateral parts (14a, 14b) and/or principal lateral parts (2a, 2b), and secondly with the complementary attachment means of the outside face of the posterior part (1).

13. Device according to claim 9, characterised in that the posterior part and/or the principal lateral parts (2a, 2b) and/or the secondary lateral parts (14a, 14b) are obtained from a longitudinally elastic fabric.

14. Device according to claim 9, characterised in that the central (4) and external (5) whalebones of the posterior part (1) are curved such that the outside face of the posterior part (1) is concave and the inside face of the said posterior part (1) that bears on the patient's lumbar vertebras is convex.

15. Device according to claim 9, characterised in that the attachment means of the outside face of the posterior part (1) and/or the principal lateral parts (2a, 2b) and/or the secondary lateral parts (14a, 14b) and the complementary attachment means (9a, 9b, 15a, 16a, 15b, 16b, 12b) consist of attachment means of the loop/hook or hook/hook type.

* * * * *